US008610085B2

(12) United States Patent
Patt

(10) Patent No.: US 8,610,085 B2
(45) Date of Patent: Dec. 17, 2013

(54) HIGH-SPEED CELLULAR CROSS SECTIONAL IMAGING

(75) Inventor: Paul Patt, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 429 days.

(21) Appl. No.: 12/859,560

(22) Filed: Aug. 19, 2010

(65) Prior Publication Data

US 2011/0204256 A1  Aug. 25, 2011

Related U.S. Application Data

(60) Provisional application No. 61/235,608, filed on Aug. 20, 2009.

(51) Int. Cl.
*F21V 9/16* (2006.01)

(52) U.S. Cl.
USPC ................................. 250/458.1; 250/461.2

(58) Field of Classification Search
CPC ................................................ G01N 21/6428
USPC ............... 250/458.1, 461.2; 382/255; 356/73, 356/338, 317; 702/19; 436/63
See application file for complete search history.

(56) References Cited

U.S. PATENT DOCUMENTS

| | | | |
|---|---|---|---|
| 3,740,560 A | 6/1973 | Wentz | |
| 4,999,513 A | 3/1991 | Ito et al. | |
| 5,055,683 A | 10/1991 | McCracken | |
| 5,528,045 A | 6/1996 | Hoffman et al. | |
| 6,344,653 B1 * | 2/2002 | Webb et al. | 250/458.1 |
| 6,591,003 B2 | 7/2003 | Chu et al. | |
| 6,636,623 B2 | 10/2003 | Nelson et al. | |
| 6,654,119 B1 * | 11/2003 | Gould et al. | 250/458.1 |
| 7,217,937 B2 * | 5/2007 | King | 250/458.1 |
| 7,450,229 B2 | 11/2008 | Ortyn et al. | |
| 2004/0021868 A1 * | 2/2004 | Ortyn et al. | 356/419 |
| 2004/0089616 A1 | 5/2004 | Kellogg et al. | |

(Continued)

FOREIGN PATENT DOCUMENTS

| | | |
|---|---|---|
| JP | 2-74846 A | 3/1990 |
| JP | 2006-501474 A | 1/2006 |
| JP | 2008-539724 A | 11/2008 |

OTHER PUBLICATIONS

International Search Report with Written Opinion mailed Oct. 20, 2010, Application No. PCT/US2010/046215, 13 pages.

(Continued)

*Primary Examiner* — Ahshik Kim
(74) *Attorney, Agent, or Firm* — Kilpatrick Townsend & Stockton LLP

(57) ABSTRACT

A cross sectional imaging system performs high-resolution, high-speed partial imaging of cells. Such a system may provide much of the information available from full imaging cytometry, but can be performed much more quickly, in part because the data analysis is greatly reduced in comparison with full image cytometry. The system includes a light source and a lens that focuses light from the light source onto a small spot in a scanning location. A transport mechanism causes relative motion between a cell in the scanning location and the spot. A sensor generates a signal indicating the intensity of light emanating from the cell as a result of illumination by the light source. The system repeatedly takes readings of the light intensity signal and characterizes the light intensity along a substantially linear path across the cell.

31 Claims, 6 Drawing Sheets

(56) References Cited

U.S. PATENT DOCUMENTS

| | | |
|---|---|---|
| 2007/0190525 A1 | 8/2007 | Gu et al. |
| 2008/0030850 A1 | 2/2008 | Wolleschensky |
| 2008/0068710 A1 | 3/2008 | Wolleschensky |
| 2008/0174842 A1 | 7/2008 | Cromwell et al. |
| 2008/0317325 A1* | 12/2008 | Ortyn et al. ................... 382/133 |

OTHER PUBLICATIONS

Mann, R.C., "Slit Scan Flow Cytometry: Separability Properties of Cell Features", Cytometry, vol. 3, No. 4, 1983, pp. 257-261.

English translation and the original Japanese Office Action from Japanese Application No. 2012-525739 mailed Aug. 6, 2013, 6 pages.

* cited by examiner

HIGH-SPEED CELLULAR CROSS SECTIONAL IMAGING

CROSS-REFERENCE TO RELATED APPLICATIONS

The present application claims the benefit of U.S. Provisional Application No. 61/235,608, filed on Aug. 20, 2009 and titled "High-speed Cellular Cross Sectional Imaging", the disclosure of which is hereby incorporated herein by reference in its entirety.

BACKGROUND OF THE INVENTION

Cytometry is a technical specialty concerned with the counting and characterization of biological cells. FIG. 1 shows a simplified diagram of one technique known as flow cytometry. In a basic form of flow cytometry, cells 101 are suspended in a fluid and entrained single-file in a narrow transparent tube 102. The entrainment can be accomplished by any of several methods, including hydrodynamic focusing. A light source 103 illuminates each cell 101 as it passes a measurement location 104. Light source 103 may be, for example, a laser. Light from light source 103 is scattered by the cell 101 being measured. Some light 105 is scattered generally in the same direction as it traveled to reach the cell 101. Light 105 is sometimes called "forward scatter", and may be collected by a forward sensor 106. Some light may be scattered in other directions as well. This light may be called "side scatter", and some of the side scattered light 107 may be collected by one or more other sensors 108. Output signals from sensors 106 and 108 are sent to a computer 109, which may store and analyze the signals. By analyzing the amount and distribution of the scattered light, it is possible to discern information about each cell, for example its size and some limited information about its internal structure.

Flow cytometry may measure the scattered light directly, or may make use of fluorescence. In fluorescence cytometry, the cells may be marked with one or more fluorophores, which are excited by light from source 103 to produce light by fluorescence. The nature of the emitted light may reveal additional information about the cells.

The technique shown in FIG. 1 relies entirely on measurements of scattered light to infer information about the cell structure, but does not produce an image of any particular cell. In another technique, called "image cytometry", an image of an individual cell may be recorded by a camera or scanning microscope. Image cytometry may provide detailed information about the cell's structure, but results in much more data than techniques that use only scattered light. Consequently, image cytometry may be relatively slow, and require the storage and analysis of large quantities of data.

BRIEF SUMMARY OF THE INVENTION

A cross sectional imaging system performs high-resolution, high-speed partial imaging of cells. Such a system may provide much of the information available from full imaging cytometry, but can be performed much more quickly, in part because the data analysis is greatly reduced in comparison with full image cytometry.

DETAILED DESCRIPTION OF THE INVENTION

Some applications for cytometry require more information than may be available from techniques based purely on scattered light, but may not require all of the information available from full image cytometry. For example, a researcher may wish to investigate whether specific biological activity occurs at the surface or nucleus of a cell, or in the cell's cytoplasm. Certain molecules may be labeled with fluorescent tags and incorporated into the cells to be studied. Many different tagging compounds, sometimes called fluorophores, are available, including the ALEXA FLUOR™ series of fluorophores available from Life Technologies Corporation of Carlsbad, Calif., USA.

Figure 1:
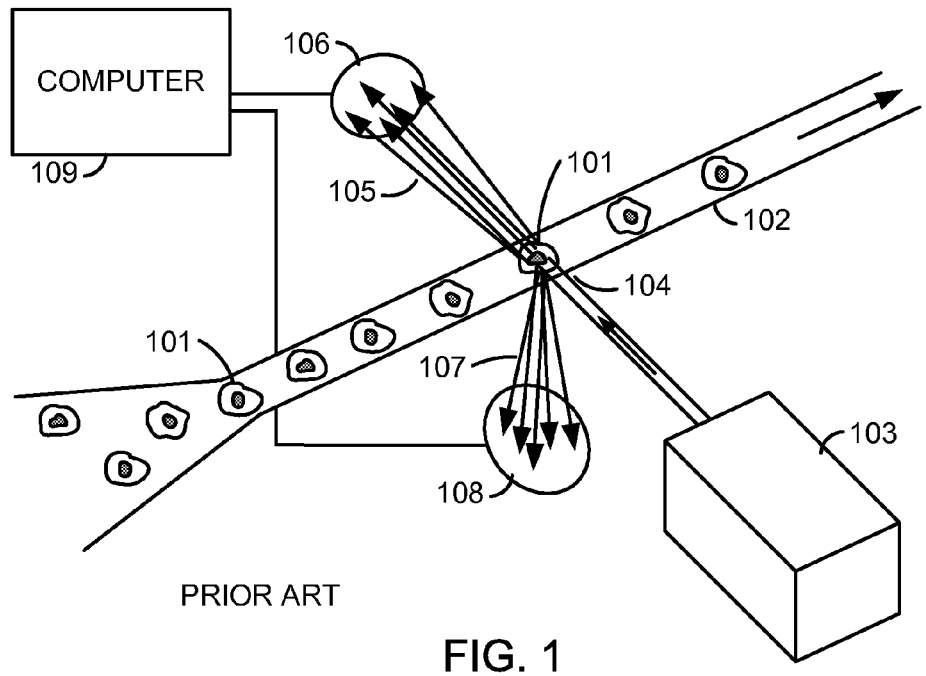
FIG. 1 shows a simplified diagram of a technique known as flow cytometry.
Figure 2:
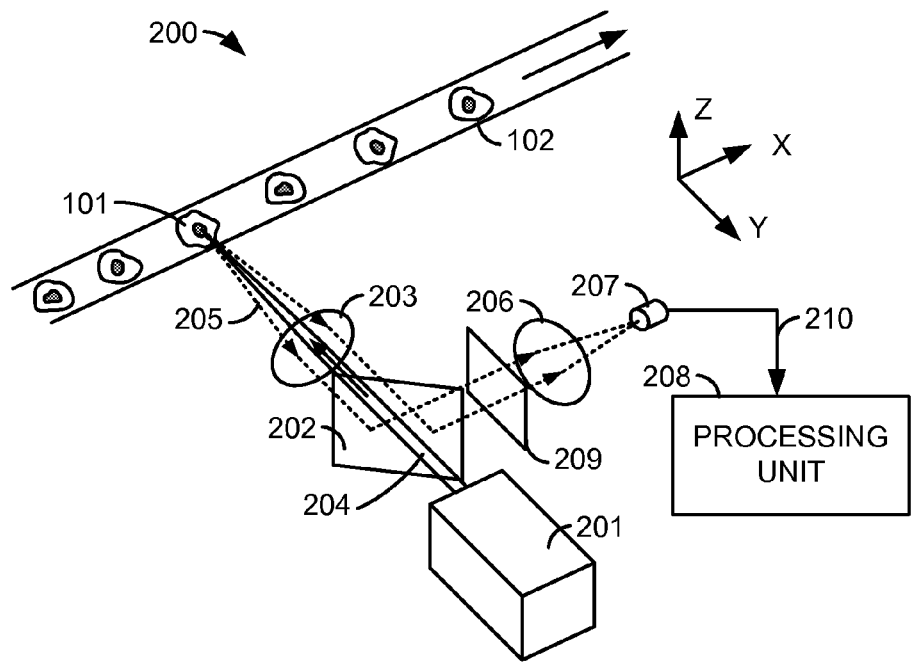
FIG. 2 shows a simplified conceptual diagram of a high-speed cross sectional cell imaging system in accordance with an embodiment.

FIG. 2 shows a simplified conceptual diagram of a high-speed cross sectional cell imaging system 200 in accordance with an embodiment. The system of FIG. 2 is a flow cytometry system, although one of skill in the art will recognize that embodiments of the invention may be utilized in other kinds of cytometry as well, including embodiments described below.

In system 200, cells 101 are entrained in fluid to progress through tube 102 in single file. The system may be used to characterize cells of many different kinds, but in a typical application, cells 101 may be, for example, about 10 to 20 micrometers across, and may progress through tube 102 at a speed of, for example, 5 to 50 millimeters per second. A light source 201 illuminates a cell through partially-reflective mirror 202 and a first lens 203. Light source 201 may be a laser that emits coherent light, or may be another kind of light source, for example a light emitting diode (LED), an arc lamp, an incandescent lamp, or another kind of light source. Light source 201 may emit coherent or non-coherent light, and may produce light continuously or may be pulsed. Partially-reflective mirror 202 may be configured, for example, to reflect the majority of light falling on it, but to transmit a portion as well. The partial reflectivity may be neutral density, in that all wavelengths are affected generally equally. Alternatively, mirror 202 may be a dichroic mirror configured to pass substantially all light at the wavelength of light source 201, and to reflect substantially all light of other wavelengths. In another embodiment, mirror 202 may simply have a hole through it to allow light from light source 201 to pass through.

Light source 201 produces a beam 204, a portion of which passes through partially-reflective mirror 202 and is focused by first lens 203 onto a small area of cell 101. (Some of the light may be reflected away from mirror 202, but is not indicated in FIG. 2.) The illuminated area of cell 101 may be, for example, only a few microns across, as compared with the unfocused diameter of beam 204, which may be hundreds or thousands of microns in diameter.

Some of the light from light source 201 may be reflected from cell 101. Additionally, a one or more fluorophore markers in cell 101 may be excited by beam 204, and may emanate light by fluorescence. Typically, the light emitted by fluorescence will be at longer wavelengths than the laser excitation light. The light 205 emanating from cell 101, whether by reflection or fluorescence, is shown in broken line in FIG. 2. Some of the emanated light 205 is gathered by first lens 203 and at least partially collimated. After passing through first lens 203, the emanated light encounters partially-reflective mirror 202, where most of it is reflected toward second lens 206. (Some of the emanated light may also pass through mirror 202, but this is not indicated in FIG. 2). An optional filter 209 may further condition light 205, for example by preferentially excluding the reflected light in favor of passing the light wavelengths emanated by fluorescence from cell 101. Second lens 206 redirects the emanated light toward a light sensor 207. Lenses 203 and 206 may form an infinity corrected optical system, allowing for the insertion of other components such as mirror 202 and filter 209 into the optical path between the lenses. Light sensor 207 converts the received light into an electrical signal 210 representing the intensity of light falling on sensor 207. The signal may be digitized and sent to a processing unit 208 for recording an analysis. In some applications, sensor 207 may be sampled, for example, at a rate of 20 to 200 kHz, resulting in a large number of samples per cell. Processing unit 208 may be a computer system, and may be stand-alone or integrated in to a testing station including the other system components.

The resolution of the system depends on the sample rate, the speed of transport of the cells past the scan location, and the light spot size on cell 101. The nominal resolution in the X direction is equal to v·dt, where v is the sample delivery speed and dt is the sampling frequency. The resolution may be more limited if the light spot size is large in relation to the nominal resolution. Preferably, v is a known parameter, either pre-determined before a particular flow experiment or measured during the course of a cell's passage through the system. Ideally, a cell being scanned should be rotation-free and jittering-free during its passage of the scan line.

Figure 3:
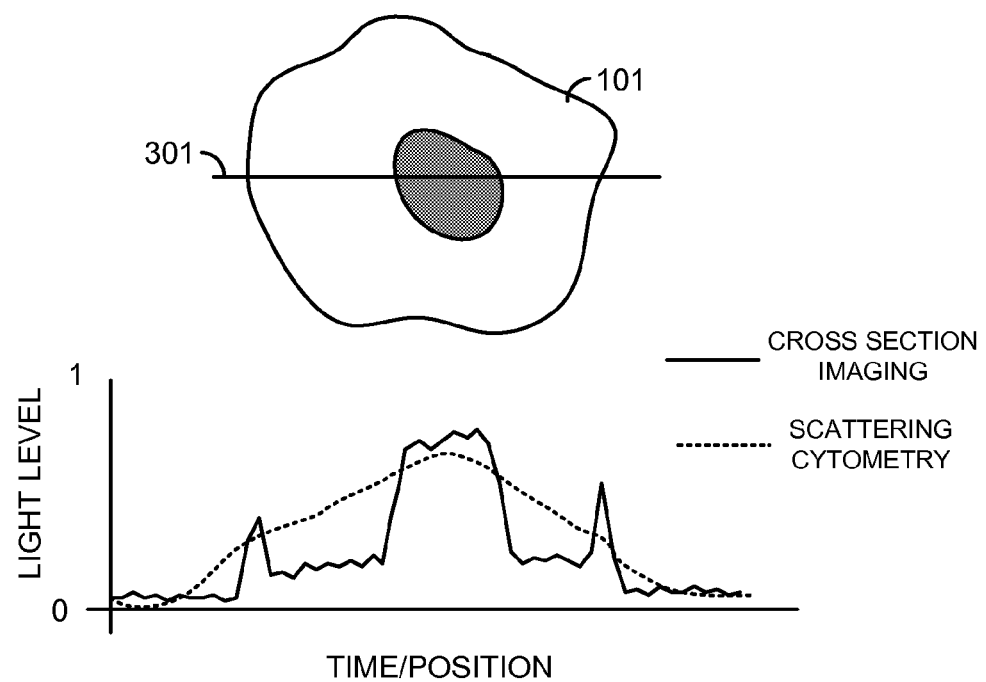
FIG. 3 illustrates an example data set representing the readings taken from one cell.

Light sensor 207 may be, for example, a photodiode, a photomultiplier tube, an avalanche photodiode, a silicon photodiode, or any other suitable kind of sensor. When signal 210 is repeatedly sampled and correlated with the movement of cell 101, the resulting data provides a high-resolution view of the light emanated from locations on or in cell 101 along a single substantially linear path. FIG. 3 illustrates an example data set representing the readings taken from one cell, along path 301, as compared with the readings that might be taken using conventional scattering-base cytometry. As is evident, the readings taken according to an embodiment of the invention, labeled "cross section imaging" in FIG. 3, provide a much more detailed view of the activity within cell 101 than is available from the data based on scattering alone.

In some experiments, the data shown in FIG. 3 may be sufficient to enable the researcher to answer the question of interest. Cross section imaging according to an embodiment of the invention may performed very rapidly, for example at a rate of thousands of cells per second. In other experiments, the cross section image data may be useful for sorting cells so that some of particular interest may be further analyzed using full imaging cytometry. The trace of FIG. 3 may be thought of as a single row of pixels from a full image scan. Such a single-row image may provide much of the information available from a full two-dimensional image of a cell, and can be acquired and processed much more quickly.

Figure 4:
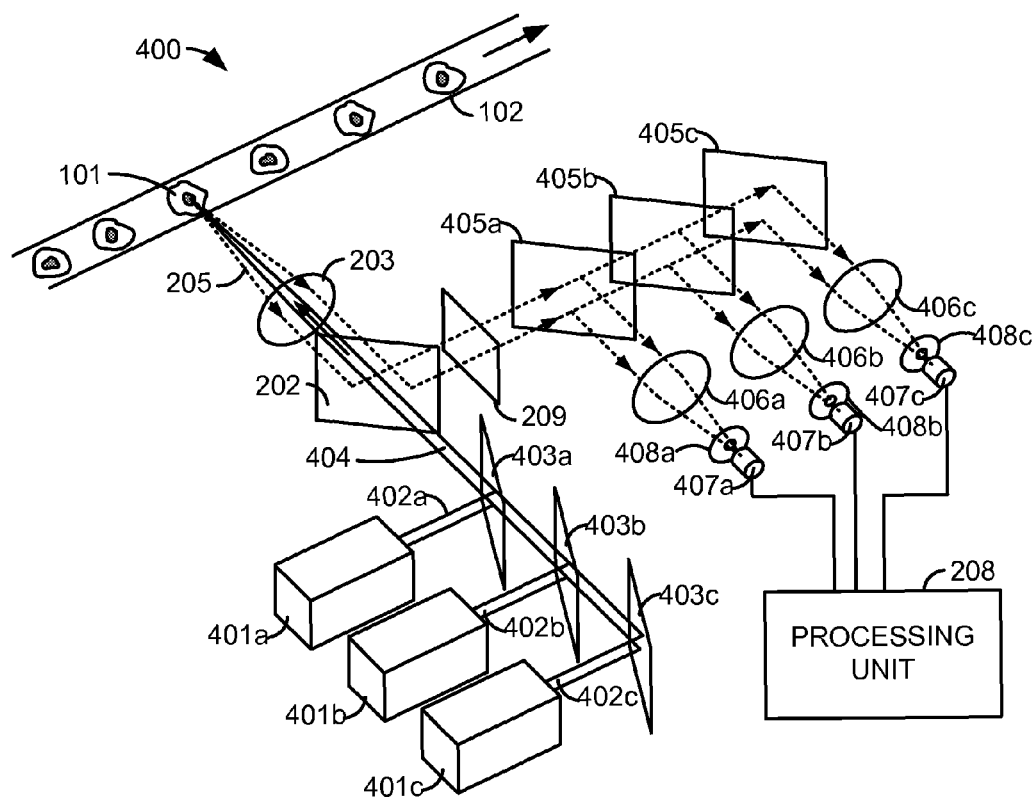
FIG. 4 illustrates a system for performing simultaneous multicolor cross section cytometry, in accordance with an embodiment.

In other embodiments, the system may be configured to perform multi-color cytometry, either using multiple excitation sources having different wavelengths, by sensing different wavelength bands of reflected or fluorescent light, or both. FIG. 4 illustrates a system 400 for performing simultaneous multicolor cross-section cytometry, in accordance with an embodiment.

In system 400, three different light sources 401a, 401b, 401c produce beams 402a, 402b, 402c, each in a narrow band of light wavelengths different from the others. For example, light sources 401a, 401b, and 401c may be different lasers. Beams 402a, 402b, and 402c reflect respectively from mirrors 403a, 403b, and 403c. In one embodiment, mirror 403c is a simple reflective mirror, while mirrors 403a and 403b are dichroic mirrors, configured to reflect substantially all of the light wavelengths produced by their respective light sources 401a and 401b, while passing substantially all of the wavelengths produced by the other light sources. The resulting composite laser beam 404 thus contains three narrow bands of wavelengths produced by the three light sources, 401a, 401b, and 401c. Composite beam 404 passes substantially through mirror 202, and is focused by lens 203 onto cell 101. The system thus has a light source that includes multiple wavelength bands. Light 205 emanating from cell 101, whether by reflection from cell 101 or as the result of fluorescence, is collected by lens 203 and at least partially collimated. The emanated light 205 mostly reflects from mirror 202 toward mirrors 405a, 405b, 405c. One or more optional filters 209 may be placed in the optical path as shown, or in another location.

Mirrors 405a and 405b are preferably dichroic mirrors, configured to preferentially reflect certain wavelength components of emanated light 205. For example, mirror 405a may reflect light in wavelengths produced by fluorescence of a first fluorophore excited by light source 401a, while mirror 405b may reflect light in wavelengths produced by fluorescence of a second fluorophore excited by light source 401b. The light reflected by mirrors 405a, 405b, and 405c passes through lenses 406a, 406b, and 406c, and reaches sensors 407a, 407b, and 407c respectively. The sensors 407a, 407b, and 407c thus receive light in different wavelength bands. For the purposes of this disclosure, wavelength bands that are different may overlap, so that some wavelengths are contained in both bands. The outputs of sensors 407a, 407b, 407c are preferably digitized and sent to processing unit 208 for storage, analysis, and display. For the purposes of this disclosure, a particular sensor and its associated components will be referred to as a "channel".

While example system 400 has been shown having three light sources 401a, 401b, 401c and three sensors 407a, 407b, 407c, one of skill in the art will recognize that other numbers of light sources, sensors, or both may be used. A system such as system 400 may be configured in many different ways. For example, mirrors 405a, 405b, and 405c may be configured to reflect light in the wavelength bands of light sources 401a, 401b, 401c, so that light reflected from cell 101 is measured. Or one or more of mirrors 405a, 405b, 405c may be configured to reflect light in the wavelength bands of respective light sources, while one or more other mirrors may be configured to preferentially reflect light in wavelengths emitted by fluorophores excited by respective light sources, so that fluorescence cross section imaging is performed. Or all three mirrors 405a, 405b, 405c may be configured to preferentially reflect light emanated from cell 101 by fluorescence. Any combination is possible. For example, one channel sensing reflected light may be used to measure the geometric limits of a particular cell, and data from channels reading light produced by fluorescence may be correlated with the geometry data to indicate where specific biologic activity is occurring. In another example, a single light source may be used to excite multiple fluorophores, so that fewer light sources are used than sensors. Other embodiments may be envisioned that include fewer sensors than light sources.

Figure 5:
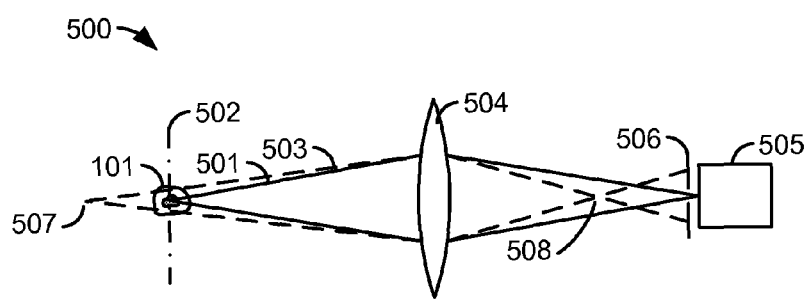
FIG. 5 illustrates semi-confocal imaging.

Any or all of the channels may optionally be configured to be confocal or semi-confocal. A confocal optical system uses an aperture placed near the sensor to preferentially exclude light emanating from locations other than in the focal plane of the system. Apertures 408a, 408b, and 408c are shown in FIG. 4, and FIG. 5 illustrates their function, in the context of a simplified optical system 500. In system 500, a first pencil of rays 501, illustrated in solid lines, emanates from focal plane 502 at cell 101. The rays are gathered by lens 504 and focused at sensor 505, after passing through aperture 506. A second pencil of rays 503, illustrated in broken lines, emanates from a point 507, removed from focal plane 502 and farther from lens 504. The rays in pencil 503 will focus at a point 508 in front of sensor 505, so that by the time the rays reach aperture 506, they are already diverged and a significant portion of the rays in pencil 503 are excluded by aperture 506 from reaching sensor 505. In this way, the system preferentially excludes rays that emanate from other than the focal plane of the system. This kind of system may produce images with higher contrast than a system without an aperture such as aperture 506. Aperture 506 may be sized or shaped in any of a variety of ways. The larger the aperture, the fewer rays are excluded, and the system may be considered to be "semi-confocal". The aperture need not be circular. For example, it could be oblong, so that its performance is different between two orthogonal axes.

In the embodiments shown thus far, relative motion is provided between the cell being evaluated and the sensing system by moving the cell past a fixed scanning location. In alternative embodiments, relative motion may be provided by moving the sensing system and holding the cell fixed, or both the sensing system and the cell may be moving, so long as relative motion between them is occurring.

Figure 6:
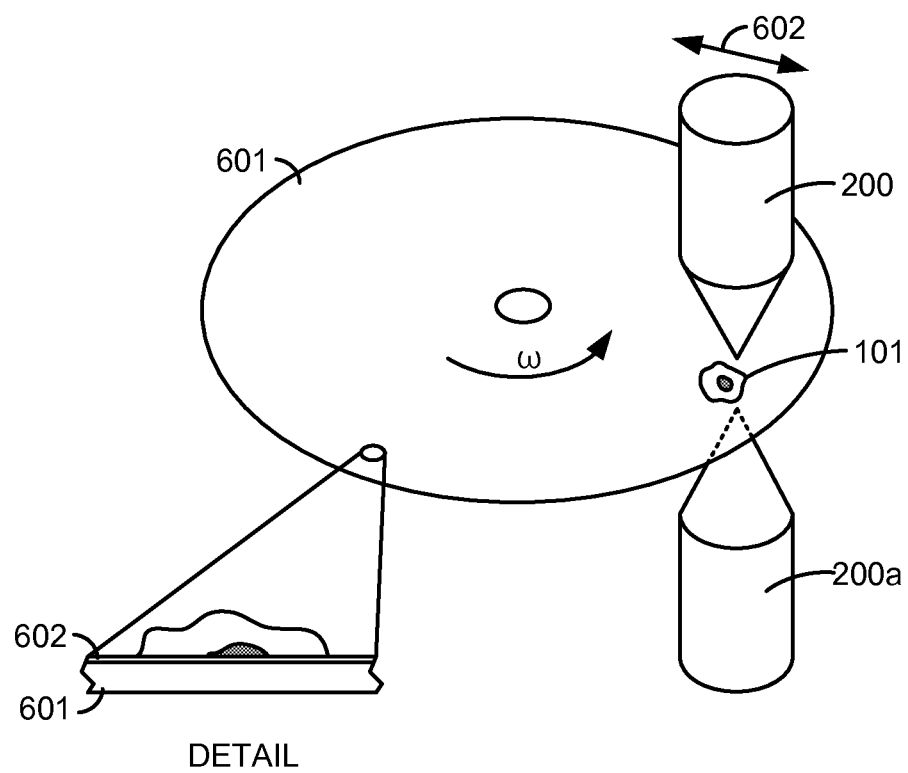
FIG. 6 shows an example system that provides rotational movement of the cells being studied, and a translational movement of the sensing system.

In another embodiment, the relative motion is provided by a rotational scanning system. FIG. 6 shows an example system 600 that provides rotational movement of the cells being studied, and a translational movement of the sensing system. In system 600, cells such as cell 101 are adhered to a rotating platen or substrate 601. Platen 601 may be, for example, a disk about 100 to 150 millimeters in diameter and made of a polymer such as polycarbonate or acrylic. Other sizes and materials may also be used. Platen 601 may be clear.

Platen 601 is rotated so that the cells are passed under an optical system such as optical system 200 shown in FIG. 2, although an optical system according to any embodiment could be used. Optical system 200 is also translatable along a generally radial path 602, so that a large portion of the surface of platen 601 is accessible for scanning by optical system 200. In this embodiment, the scanning path across any particular cell will be an arc of a circle. However, the radius of the arc is very large in comparison with the dimensions of any particular cell, and the path across a single cell may be considered essentially linear. Using a system such as system 600, a large number of cells may be characterized by systematically scanning the platen with coordinated translation of the optical system and rotation of the platen, in much the same way that a compact disc (CD) or digital versatile disc (DVD) is read by an audio or video system. The platen 601 may be "read" from the top, as by optical system 200, or from the bottom by alternate optical system 200a.

In some embodiments, platen 601 may be scanned or otherwise accessed from both sides in a coordinated manner. For example, optical systems 200 and 200a may both scan the cells adhered to plate 601. The two optical systems may scan using different excitation wavelengths, different filtration of the light emanated from the cells being measured, or both.

In another embodiment, if a measurement of a particular cell made from the top of platen 601 indicates that the cell may exhibit an activity or characteristic that warrants further study, the cell may be liberated from the platen 601 by a burst of light delivered from the bottom of platen 601. As is shown in the detail view in FIG. 6, the top surface of platen 601 may include a wavelength-selective fusible surface 602, that releases a cell adhered to it when subjected to light in a particular wavelength. The liberated cells may be washed from the surface of platen 601 and collected for more detailed analysis, for example by full imaging cytometry or microscopic examination.

Figure 7:
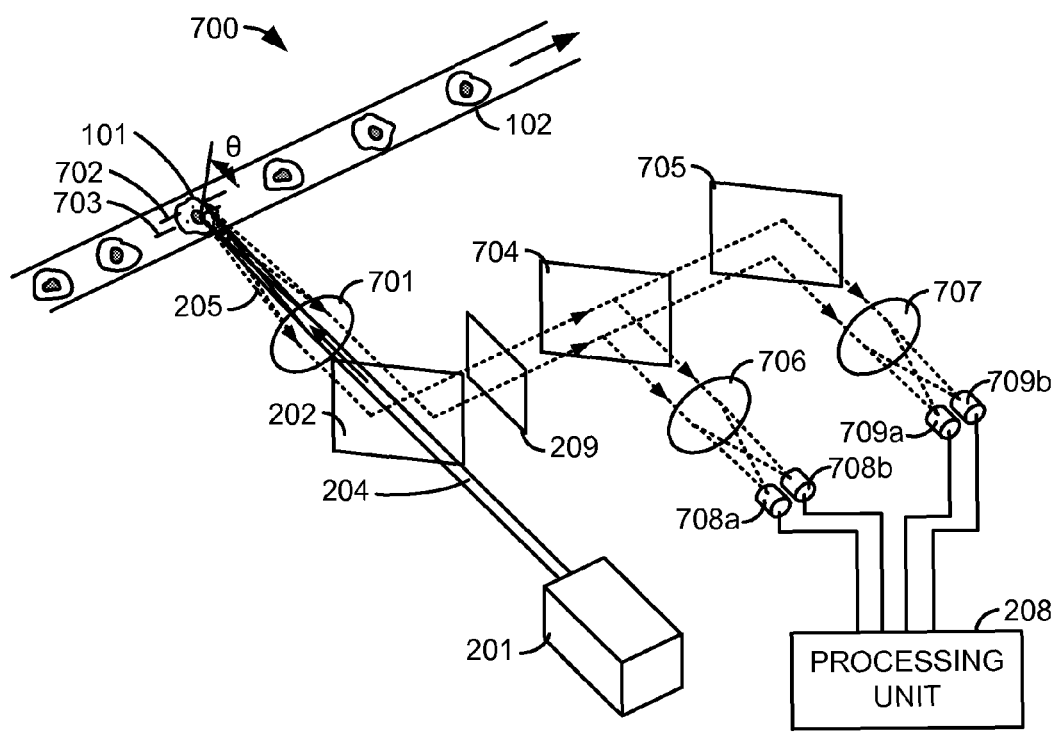
FIG. 7 illustrates a system for performing simultaneous multi-line cross sectional imaging, in accordance with another embodiment.

FIG. 7 illustrates a system for performing simultaneous multi-line cross sectional imaging, in accordance with another embodiment. In some applications, it may be helpful to scan multiple traces across each cell. For example, one cross section image may be gathered across the approximate center of each cell, and another image gathered near the periphery of the cell. If the two images are gathered with the same resolution, this nominally doubles the amount of information gathered from each cell, but still results in much less data than full imaging cytometry. Other numbers of traces may be gathered, for example, three, four, or any another number, but preferably five or fewer. Similarly, the traces need not all be of the same resolution.

In the example of FIG. 7, a light source 201 generates a collimated beam 204, which passes substantially through partially reflective mirror 202 and encounters lens 701. In contrast to previous embodiments, lens 701 is a multifaceted "fly's eye" lens, a diffractive lens, a holographic lens, or another kind of optical system that splits beam 204, focusing portions of beam 204 on two different spots at cell 101. The two spots are displaced from each other, so that they trace displaced parallel paths 702, 703 across cell 101 as cell 101 is transported by the scanning area. The displacement of the spots is in a direction oriented at an angle θ from the direction of travel of cell 101. Preferably, θ is greater than zero degrees, and may be about 90 degrees. (If θ=0, no additional information is gathered about cell 101 as compared with single line cross sectional image, but cell 101 may be double sampled, enabling construction of a cross section image with reduced noise.)

Light 205 emanates from the illuminated spots on cell 101, whether by reflection or fluorescence or both, and is gathered and at least partially collimated by lens 701. The light substantially reflects from mirror 202, may encounter a filter 209 and mirrors such as mirrors 704 and 705, and eventually reaches lenses 706 and 707. (The path of light 205 between lens 701 and lenses 705 and 707 is simplified in FIG. 7.) Mirrors 704 and 705 may be, for example, dichroic mirrors that preferentially separate different bands of wavelengths from light 205 to be directed to lenses 706 and 707. Lenses 706 and 707 preferably cooperate with lens 701 to form an infinity corrected optical system, allowing for the insertion of mirrors, filters, or other components between them. Like lens 701, lenses 706 and 707 may be multifaceted "fly's eye" lenses, diffractive lenses, holographic lenses, or other optical systems that displace portions of the light reaching them, directing images to two sets of sensors 708a and 708b, and 709a and 709b. The respective images correspond to the two spots illuminated on cell 101. The signals produced by sensors 708a, 708b, 709a, and 709b are passed to processing unit 208 for storage, analysis, display or the like.

The system of FIG. 7 thus scans cross section images along two separated paths 702, 703 on cell 101. For each path, images are scanned in two wavelength bands. One of skill in the art will recognize that system 700 could be adapted to use multiple sources of illumination, such as multiple lasers emitting light in different wavelength bands, and could be adapted to scan pairs of images in fewer or more wavelength bands.

Figure 8:
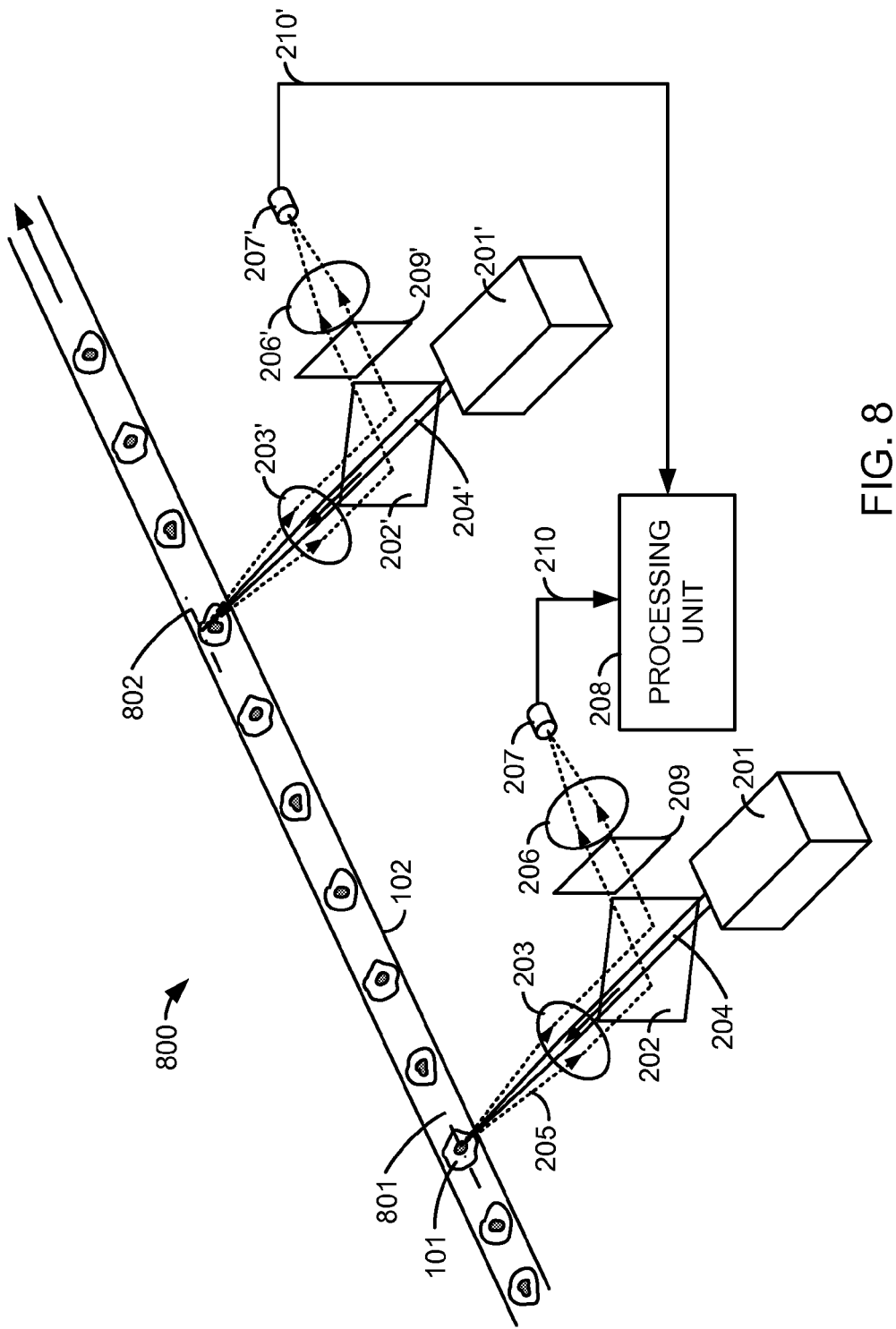
FIG. 8 illustrates a system for performing multi-line cross sectional imaging, in accordance with another embodiment.

FIG. 8 shows a system 800 for performing multi-line cross sectional imaging, in accordance with another embodiment. In this embodiment, rather than using optical means to split the illumination light and light emanating from the measured cell, two cross section imaging systems are placed along the flow path with a lateral displacement, so that one path across a cell is imaged by the first optical system at a first time, and a different path across the cell is imaged by a different optical system at a later time. In system 800, two optical systems like those of FIG. 2 are shown providing signals to a processing unit 208 for storage, analysis, display, or the like. More than two systems could be used. While the system of FIG. 2 utilizes only one excitation source 201 and one sensor 207, one of skill in the art will recognize that system 800 could easily be adapted to use more excitation sources, sensors, or both. For example, system 800 could be adapted to use two or more of the optical system of FIG. 4.

The first optical system in system 800 illuminates cell 101 with light source 201, eventually resulting in light that is sensed by sensor 207. The system is aligned to scan cell 101 along a path 801, which in this example is near the center of the cell. The second optical system (denoted with primed reference numbers) illuminates passing cells in a second scanning location with light source 201', resulting in light that is sensed by sensor 207'. The second optical system is aligned to scan cells along path 802, which in this example is near the edge of each passing cell. Any particular cell 101 is scanned by both optical systems, but not simultaneously. Processing unit 208 may store the results the first cross sectional imaging and correlate them with the results of the second imaging, to create a set of cross section images of each cell.

While embodiments of the invention have been illustrated as scanning cells confined in a linear tube or adhered to a rotating substrate, one of skill in the art will recognize that embodiments of the invention may be utilized in systems using any of a wide range of cell delivery techniques, including electrophoresis, pressure driven flow, optical tweezers, motorized translation stage, and others. Cells may be conveyed as a payload in an oil emulsion, in an electrowetting-actuated droplet, or via magnetic transport assisted by magnetic bead tagging. It is intended that the claims not be limited by the cell delivery method utilized.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A system for performing cytometry, the system comprising:
   a light source;
   a lens that focuses light from the light source onto a spot in a scanning location;
   a transport mechanism that causes relative motion between a cell in the scanning location and the spot;
   a sensor that indicates the intensity of light emanating from the cell as a result of illumination by the light source, wherein the lens gathers light emanating from the cell for direction to the sensor; and
   a processing unit that repeatedly takes readings of the light intensity indication and characterizes the light intensity along a substantially linear path across the cell, wherein the resolution of the system is dependent on the size of the spot.

2. The system of claim 1, wherein the light source comprises at least one laser.

3. The system of claim 1, wherein the light source comprises at least one light source selected from the group consisting of a coherent light source, a non-coherent light source, a continuous light source, and a pulsed light source.

4. The system of claim 1, wherein the sensor indicates at least in part the intensity of light emanating from the cell by reflection of light from the light source.

5. The system of claim 1, wherein the sensor indicates at least in part the intensity of light emanating from the cell as a result of fluorescence excited by the light source.

6. The system of claim 1, wherein the cell is suspended in a fluid and transport mechanism transports the cell past the scanning location by flow of the fluid.

7. The system of claim 1, further comprising a rotating substrate on which the cell is adhered.

8. The system of claim 1, further comprising an aperture proximate the sensor, such that the system performs semi-confocal imaging.

9. The system of claim 1, wherein the light source produces light in at least first and second wavelength bands.

10. The system of claim 1, wherein the light sensor is a first light sensor, the system further comprising a second sensor, and wherein the first and second sensors receive light in different wavelength bands.

11. The system of claim 1, wherein the sensor is selected from the group consisting of a photodiode, a photomultiplier tube, an avalanche photodiode, a silicon photodiode.

12. A system for performing cytometry, the system comprising:
   a light source;
   an optical system that focuses light from the light source onto at least two spots in a scanning location, the spots being displaced from each other;
   a transport mechanism that causes relative motion between a cell in the scanning location and the at least two spots;
   a set of at least two sensors, each sensor indicating the intensity of light emanating from the cell as a result of illumination by the light source at a respective one of the spots, wherein the optical system at least in part gathers light emanating from the cell for direction to at least one of the sensors; and
   a processing unit that repeatedly takes readings of the light intensity indications from the at least two sensors and characterizes the light intensity along at least two displaced substantially linear paths across the cell traced by the at least two spots, wherein the resolution of the system is dependent on the sizes of the spots.

13. The system of claim 12, wherein the optical system comprises at least one member selected from the group consisting of a multi-faceted lens, a diffractive lens, and a holographic lens.

14. The system of claim 12, wherein the set of at least two sensors is a first set, the system further comprising a second set of at least two sensors each indicating the intensity of light emanating from the cell as a result of illumination by the light source at a respective one of the spots, wherein the two sets of sensors receive light in different wavelength bands.

15. The system of claim 12, wherein the light source comprises at least one laser.

16. The system of claim 12, wherein the light source comprises at least one light source selected from the group consisting of a coherent light source, a non-coherent light source, a continuous light source, and a pulsed light source.

17. The system of claim 12, wherein at least one sensor indicates at least in part the intensity of light emanating from the cell by reflection of light from the light source.

18. The system of claim 12, wherein at least one sensor indicates at least in part the intensity of light emanating from the cell as a result of fluorescence excited by the light source.

19. A system for performing cytometry, the system comprising:
    at least two light sources;
    at least two optical systems, each optical system focusing light from one of the light sources onto a respective spot in one of at least two respective scanning locations;
    a transport mechanism that causes relative motion between a cell and the scanning locations, such that the cell passes sequentially through the at least two scanning locations; and
    at least two sensors, each sensor indicating the intensity of light emanating from a cell as a result of illumination by the light sources as the cell passes each respective scanning location, wherein the optical systems at least in part gather light emanating from the cell for direction to the sensors;
    wherein the optical systems are aligned such that each spot traces a different substantially linear path across the cell, and the system further comprises a processing unit that repeatedly takes readings of the light intensity indications from the at least two sensors and characterizes the light intensity along the respective substantially linear paths, and wherein the resolution of the system is dependent on the sizes of the spots.

20. The system of claim 19, wherein at least one of the two light sources comprises at least one laser.

21. The system of claim 19, wherein at least one of the two light sources comprises at least one light source selected from the group consisting of a coherent light source, a non-coherent light source, a continuous light source, and a pulsed light source.

22. The system of claim 19, wherein at least one of the sensors indicates at least in part the intensity of light emanating from the cell by reflection of light from the light source.

23. The system of claim 19, wherein at least one of the sensors indicates at least in part the intensity of light emanating from the cell as a result of fluorescence excited by the light source.

24. A method of performing cytometry, the method comprising:
    focusing, using an optical system comprising a lens, light from a light source onto a spot in a scanning location;
    creating, via a transport mechanism, relative motion between a cell in the scanning location and the spot;
    gathering, using the lens, light emanating from the cell as a result of illumination by the light source;
    directing the gathered light to a sensor;
    sensing the intensity of the light reaching the sensor; and
    using a computerized processing unit, repeatedly taking readings of the light intensity indication and characterizing the light intensity along a substantially linear path across the cell, wherein the resolution of a system employing the method is dependent on the size of the spot.

25. The method of claim 24, wherein focusing light from a light source comprises focusing light generated by at least one laser.

26. The method of claim 24, wherein focusing light from a light source comprises focusing light generated by at least one light source selected from the group consisting of a coherent light source, a non-coherent light source, a continuous light source, and a pulsed light source.

27. The method of claim 24, wherein sensing the intensity of light emanating from the cell comprises sensing the intensity of light reflected from the cell.

28. The method of claim 24, wherein sensing the intensity of light emanating from the cell comprises sensing the intensity of light emanating from the cell as a result of fluorescence excited by the light source.

29. The method of claim 24, further comprising:
    suspending the cell in a fluid; and
    transporting the cell past the scanning location by flow of the fluid.

30. The method of claim 24, wherein sensing the intensity of light emanating from the cell comprises sensing the intensity of light in at least two wavelength bands.

31. The method of claim 24, wherein the sensor is selected from the group consisting of a photodiode, a photomultiplier tube, an avalanche photodiode, a silicon photodiode.

* * * * *